US007125716B2

(12) United States Patent
Nakano et al.

(10) Patent No.: US 7,125,716 B2
(45) Date of Patent: Oct. 24, 2006

(54) CULTURABLE MITOCHONDRIAL CELLS WITH NO NUCLEUS, SHOWING MITOCHONDRIAL ACTIVITY

(75) Inventors: Kazutoshi Nakano, Tokyo (JP); Shigeo Ohta, Kawasaki (JP)

(73) Assignee: Eisai Research Institute, Tokyo (JP)

( * ) Notice: Subject to any disclaimer, the term of this patent is extended or adjusted under 35 U.S.C. 154(b) by 0 days.

(21) Appl. No.: 10/438,279

(22) Filed: May 14, 2003

(65) Prior Publication Data

US 2004/0121458 A1  Jun. 24, 2004

(30) Foreign Application Priority Data

May 15, 2002  (JP) ............................ 2002-139673
May 9, 2003  (JP) ............................ 2003-131993

(51) Int. Cl.
  *C12N 5/16* (2006.01)
  *C12N 5/22* (2006.01)
  *C12N 5/02* (2006.01)
(52) U.S. Cl. .................... 435/346; 435/325; 435/317.1
(58) Field of Classification Search ................ 435/325, 435/346, 383, 395
  See application file for complete search history.

(56) References Cited

U.S. PATENT DOCUMENTS

2003/0159167 A1*  8/2003  Hayashi ........................ 800/18

OTHER PUBLICATIONS

Aomi et al. Cytoplasmic transfer of platelet mDNA from elderly patients with Parkinson's disease to mtDNA-less HeLa cells restores complete mitochondrial respiratory function. Biochem Biophys Res Commun. vol. 280, No. 1, pp. 265-273. Jan. 2001.*
Keeton et al. Biological Science, 5th edition. London: W.W. Norton & Company, Inc., 1993, pp. 125-129 and 873-874.*
Nakano et al. Continuous culture of novel mitochondrial cells lacking nuclei. Mitochondrion, vol. 3, No. 1, pp. 21-27, Aug. 2003.*
Prescott et al. Mass Enucleation of Cultured Animal Cells. Methods Cell Biol. vol. 7, pp. 189-202, 1973.*
Anderson, et al., "Sequence and Organization of the Human Mitochrondrial Genome", *Nature*, 290: 457-465, 1981.
Campos, et al., "Leigh Syndrome Associated with the T9176C Mutation in the ATPase 6 Gene of Mitochondrial DNA", *Neurology*, 49: 595-597, 1997.
Chomyn, et al., "Melas Mutation in mtDNA Binding Site for Transcription Termination Factor Causes Defects in Protein Synthesis and in Respiration But No Change in Levels of Upstream and Downstream Mature Transcripts" *Proc. Natl. Acad. Sci USA*, 89: 4221-4225, 1992.
Dunbar, et al., "Complex I Deficiencey is Associated with 3243G:C Mitochondrial DNA in Osteosarcoma Cell Cybrids" *Hum. Mol. Genet*. 5: 123-129, 1996.
Frey, T., "Nucleic Acid Dyes for Detection of Apoptosis in Live Cells", *Cytometry*, 21:265-274, 1995.

Grunewald, et al., "Bioenergetics in Huntingdon's Disease", *Ann New York Academy, Science*, 893: 203-213, 1999.
Haas, et al., "Low Platelet Mitochondrial Complex I and Complex II/III Activity in Early Untreated Parkinson's Disease" *Ann. Neurol*, 37:714-722, 1995.
Hollinshead, et al., "Anti-Biotin Antibodies Offer Superior Organelle-Specific Labeling of Mitochondria over Avidin or Streptavidin" *J. Histochem. Cytochem*, 45: 1053-1057, 1997.
Ligon, et al., "Movement of Mitochondria in the Axons and Dendrites of Cultured. Hippocampal Neurons", *J. Comp Neurol*, 427: 340-350, 2000.
Makino, et al., "Confirmation that a T-to-C Mutation of9176 in Mitochondrial DNA is an Additional Candidate Mutation for Leigh's Syndrome" *Neuromuscular Dis*, 8:149-151, 1998.
Maurer, et al., "A Selective Defect of Cytochrome c Oxidase is Present in Brain of Alzheimer Disease Patients", *Neurobiology of Aging*, 21: 455-462, 2000.
Shoffner, et al., "Mitochondrial DNA Variants Observed in Alzheimer Disease and Parkinson Disease Patients", *Genomics*, 17: 171-184, 1993.
Shults, et al., "Absorption, Tolerability, and Effects on Mitochondrial Activity of Oral Coenzyme $Q_{10}$ in Parkinsonian Patients" *Neurology*, 50: 193-195, 1998.
Stumpf, et al., "Loosely Coupled Mitochondrial Oxidative Phosphorylation Induced by Protoporphyrin", *Biochem Med*. 21: 182-189, 1979.
Thyagarajan, et al., "A Novel Mitochondrial ATPase 6 Point Mutation in Familial Bilateral Striatal Necrosis", *Ann Neurol*, 38(3): 468-472, 1995.
Hatefi, et al., "Studies on the Electron Transport System", XXXII. Respiratory Control in Beef Heart Mitochondria, Archives of Biochemistry and Biophysics, 94: 148-155, 1961.
Chomyn, et al., "Platelet-Mediated Transformation of mtDNA-Less Human Cells: Analysis of Phenotypic Variability Among Clones from Normal Individuals—and Complementation Behavior of the $tRNA^{Lys}$ Mutation Causing Myoclonic Epilepsy and Ragged Red Fibers", *Am. J. Hum Genet*. 54: 966-974, 1994.
Gu, et al., "Mitochondrial DNA Transmission of the Mitochondrial Defect in Parkinson's Disease", *Ann. Neurol*. 44: 177-186, 1998.
Hatafi, et al., "Studies on the Electron Transport System. XXXII. Respiratory Control in Beef Heart Mitochondria", *Archives of Biochemistry and Biophysics*, 94: 148-155. 1961.
Lai, et al., "Preparation of Synaptic and Nonsynaptic Mitochondria from Mammalian Brain", *Methods in Enzymology*, IV: 51-59, 1979.

* cited by examiner

*Primary Examiner*—Celian Qian
*Assistant Examiner*—Jennifer Dunston
(74) *Attorney, Agent, or Firm*—Choate, Hall & Stewart, LLP

(57) ABSTRACT

Provided are a method of producing a culturable cell with no nucleus, showing mitochondrial activity, comprising: performing cell fusion between a nucleus-less cell having mitochondrial DNA and a mitochondrial DNA-less cultured cell derived from a cancer cell; culturing resulting cybrid cells; and recovering floating cells from obtained cultured cells, and a cell obtained by the method.

5 Claims, 5 Drawing Sheets

A.

B.

A.

B.

C.

D.

E.

F.

G.

H.

I.

J.

K.

L.

M.

N.

O.

P.

Q.

R.

S.

T.

A.

B.

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:PCR Primer

<400> SEQUENCE: 1
ggccacctac tcatgcacct aa                                              22

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:PCR primer.

<400> SEQUENCE: 2
gtgttgtcgt gcaggtagag gcttcct                                         27

CULTURABLE MITOCHONDRIAL CELLS WITH NO NUCLEUS, SHOWING MITOCHONDRIAL ACTIVITY

BACKGROUND OF THE INVENTION

The present invention relates to novel culturable cells with no nucleus, showing mitochondrial activity.

Amitochondrion has its own DNA (mitochondrial DNA: hereinafter, referred to also as "mtDNA") and an autonomous genetic expressing system. Only 13 peptides, however, are encoded by mtDNA and all the other mitochondrial proteins including factors relating to the genetic expression system are encoded by nuclear genes. Therefore, it has been believed that mitochondria will not be maintained without nucleus. Conventionally, techniques for isolating and purifying mitochondria from liver, heart muscle, skeletal muscle, brain, platelets and so on have been established (cf. non-patent documents 1–3). Functions of mitochondria, such as enzyme activity, have been evaluated with purified mitochondria in various diseases including mitochondrial diseases, Parkinson's disease, Alzheimer's disease, and Huntington disease (cf. non-patent documents 3–6). However, isolated and purified mitochondria have no proliferation potency so that it is impossible to culture the mitochondria.

Platelets are unique cells in an organism. They separate from megakaryocytes and have mitochondria but no nucleus. However, platelets have no proliferation potency and their life lasts only several days in an organism. This has made it impossible to observe changes of mitochondria with passage of time.

On the other hand, mtDNA-less human cell lines, designated $Rho^0$ cells, have been isolated (cf. non-patent document 7). Fusion of cells of a $Rho^0$ cell line with enucleated cells having mutant mtDNA to effect cytoplasmic transfer has enabled culture of cells having the mutant mtDNA (cybrids) Cell lines, obtained by fusing $Rho^0$ cells with enucleated cells from patients with a variety of mitochondrial diseases, have contributed to elucidation of mitochondrial disorders (cf. non-patent documents 8–10). However, the mitochondria of such a cybrid cell are always under the influence of the nucleus and there is the possibility that the change of mitochondria in cultured cells when a drug is administered to the cultured cells is attributable to an indirect action of the drug to the mitochondria through the nucleus. Accordingly, such cybrid cells have been unsatisfactory for the evaluation of direct action of a drug or the like to mitochondria. From those facts, it has been demanded to culture cells that have no nucleus and show mitochondrial activity governed by mitochondria.

<Non-Patent Document 1>
Stumpf et al. Biochem Med 21, 182–189, 1979

<Non-Patent Document 2>
Hatafi Y et al. A.B.B. 94 148, 1964. Methods in enzymology IV, 51–59, 1979

<Non-Patent Document 3>
Haas R H, K Nakano et al. Ann Neurol 1995; 37: 714–722

<Non-Patent Document 4>
Shoffner J M, Brown M D, et al. Genomics 17: 171–184, 1993

<Non-Patent Document 5>
Grunewald T et al. Ann New York Academy Science 893: 203–213, 1999

<Non-Patent Document 6>
Maurer I et al. Neurobiology of Aging 21: 455–62, 2000

<Non-Patent Document 7>
GuM Cooper J M et al. Ann Neurol 44: 177–186, 1998

<Non-Patent Document 8>
Chomyn A, et al. Proc Natl Acad Sci USA 89: 4221–4225, 1992

<Non-Patent Document 9>
Dunbar D R, et al. Hum Mol Genet 5: 123–129, 1996

<Non-Patent Document 10>
Chomyn A, et al. Am J Hum Genet 34: 966–974, 1994

SUMMARY OF THE INVENTION

As a result of extensive studies with a view to achieving the above-mentioned object, the inventors of the present invention have been successful in providing culturable cells with no nucleus, showing mitochondrial activity by cell fusion of nucleus-less cells having mitochondrial DNA with mtDNA-less cultured cells derived from cancer cells, culturing the resultant cybrid cells and recovering floating cells from obtained cultured cells, thereby achieving the present invention.

The present invention has been made as described above and the subject matter of the present invention is as follows.

(1) A method of producing a culturable cell with no nucleus, showing mitochondrial activity, comprising:
performing cell fusion between a nucleus-less cell having mitochondrial DNA and a mitochondrial DNA-less cultured cell derived from a cancer cell;
culturing resulting cybrid cells; and
recovering floating cells from obtained cultured cells.

(2) A method according to the item (1), in which the nucleus-less cell having mitochondrial DNA is a platelet.

(3) A method according to the item (1), in which the mitochondrial DNA-less cultured cell derived from a cancer cell is a Hela $Rho^0$ cell.

(4) A culturable cell with no nucleus, showing mitochondrial activity obtained by the method according to any one of the items (1) to (3).

(5) A method of screening a therapeutic drug for a mitochondria-associated disease, comprising administering testing drugs to cells according to the item (4) and screening the drugs using mitochondrial activity of the cells as an index.

(6) A method according to the item (5), in which the mitochondria-associated disease is one selected from mitochondrial disease, Alzheimer dementia and Parkinson's disease.

BRIEF EXPLANATION OF THE DRAWINGS

FIG. 2A shows cells that were stained with hematoxylin-eosin at a magnification of 20×. FIG. 2B shows the original cybrid cells stained nucleus with hematoxylin-eosin at a magnification of 20×.

FIG. 3A shows a wild type floating cells stained with MitoTracker fluorescent dye.

(magnification 60×). FIG. 3B shows a transparent microscopy image of a floating cell. FIGS. 3C—3J show staining of wild type, and mutant cybrids and floating cells with Mitotracker and Mitotracker Green. FIG. 3C shows staining of wild type floating cells with MitoTracker. FIG. 3D shows staining of wild type floating cells with MitoTracker Green. FIG. 3E shows staining of the mitochondria of wild type cybrids labeled with MitoTracker. FIG. 3F shows staining of the mitochondria of wild type cybrids labeled with MitoTracker Green. FIG. 3G shows staining of mutation type floating cells with MitoTracker. FIG. 3H shows staining of mutation type floating cells with MitoTracker Green. FIG. 3I shows staining of the mitochondria of mutation type cybrids labeled with MitoTracker. FIG. 3J shows staining of the mitochondria of mutation type cybrids labeled with MitoTracker Green. FIGS. 3K-3T shows double staining of wild type floating cells and the mutation type floating cells labeled with MitoTracker and SYTO Green dyes (magnification 100×). FIG. 3K shows staining of wild type floating cells labeled with MitoTracker. FIG. 3L shows lack of staining of wild type floating cells labeled with SYTO Green. FIG. 3M shows transmission microscopy of the surface of wild type floating cells. FIG. 3N shows staining of wild type cybrids labeled with MitoTracker. FIG. 3O shows staining of wild type cybrids labeled with SYTO Green. FIG. 3P shows staining of mutation type floating cells with MitoTracker. FIG. 3Q shows lack of staining of mutation type floating cells labeled with SYTO Green. FIG. 3R shows transmission microscopy of the surface mutation type floating cells. FIG. 3S shows staining of mutation type cybrids labeled with MitoTracker. FIG. 3T shows staining of mutation type cybrids labeled with SYTO Green.

FIG. 4A shows mitochondrial mutation type cells. FIG. 4B shows mitochondrial wild type cells. FIG. 4C shows mutation type cybrids. FIG. 4D shows wild type cybrids. FIG. 4E shows a curve quantifying the intensity of cell staining with MitoTracker. The left open curve is the intensity of the mutation type mitochondrial cells. The right closed black curve is that of the wild type cells. FIG. 4F shows a curve quantifying the intensity of cybrid staining with MitoTracker. The left open curve is the intensity of the mutation type cybrids. The right closed black curve is that of the wild type cybrids.

DETAILED DESCRIPTION OF THE INVENTION

Figure 1:
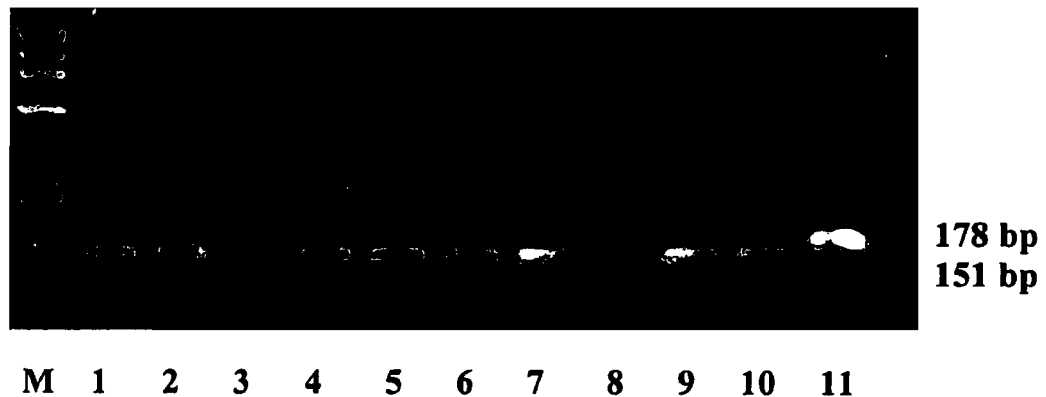
FIG. 1 is a diagram (photograph) showing results of restricted fragment length analysis of T9176C mutation in novel mitochondrial cells.

Hereinafter, the present invention will be described in detail.

(1) Method of Producing the Cells of the Present Invention

The present invention relates to a method of producing a culturable cell with no nucleus, showing mitochondrial activity, comprising: performing cell fusion between a nucleus-less cell having mitochondrial DNA and a mitochondrial DNA-less cultured cell derived from a cancer cell; culturing resulting cybrid cells; and recovering floating cells from obtained cultured cells. Hereinafter, a culturable cell with no nucleus, showing mitochondrial activity is also referred to as a "mitochondrial cell."

The nucleus-less cell having mitochondrial DNA used in the method of the present invention may be a cell that is produced by enucleating a cell that has a nucleus and mitochondrial DNA or a cell that genetically lacks a nucleus but has mitochondrial DNA. It is preferred that the cell that genetically lacks a nucleus but has mitochondrial DNA be used. Examples of such a cell include platelets.

The cell that lacks a nucleus but has mitochondrial DNA can be obtained from an organism that has mitochondrial DNA in the cell. As such an organism, mammals are preferred with human being particularly preferred.

In the method of the present invention, use of cells obtained from patients with mitochondria-associated diseases from whom informed consents were obtained in advance as the cells that lack a nucleus but have mitochondrial DNA can provide mitochondrial cells each having a mutation of mitochondrial disease. Examples of mitochondria-associated diseases include mitochondrial diseases such as Leigh syndrome, Alzheimer's disease and Parkinson's disease.

The mtDNA-less cultured cells derived from cancer cells that are used in the method of the present invention include known $Rho^0$ cell lines that have a nucleus but no mtDNA. Specific examples thereof include Hela $Rho^0$ cell line, fibroblast $Rho^0$ cell line, and osteosarcoma $Rho^0$ cell line. Among those, Hela $Rho^0$ cell line is preferable. Note that cultured cells derived from cancer cells may be either those cells obtained by culturing a cell derived from a cancer tissue in an organism or those cells obtained by culturing a cell derived from an established cell line obtained by cancerizing a cell derived from normal tissue in an organism.

In the method of the present invention, cell fusion may be performed according to usual cell fusion techniques for preparing cybrids.

Specifically, for example, cell fusion can be performed by adding mtDNA-less cultured cells derived from cancer cells to nucleus-less cells each having mtDNA that serve as mitochondria donors and allowing cell fusion in the presence of ethylene glycol or the like.

Culture of the obtained cybrid cells can be performed by usual cell culture means.

Specifically, for example, the culture of cybrid cells can be performed in a Dulbecco's modified Eagle medium (D-MEM) containing 10% fetal bovine serum (FBS) at 37° C. in a humidified gas mixture containing 8% $CO_2$. The culture may be performed for 7 to 30 days, preferably 14 to 30 days.

Cybrid cells initially proliferate in an adherent form, followed by the proliferating cell overlying the adherent cells. The overlying cells are separated from the adherent cells and float in the medium as overgrowth proceeds. The term "floating cells" as used herein means those cells that float in the medium.

Recovery of the floating cells can be performed by, for example, recovery of supernatant of the medium.

(2) Mitochondrial Cells of the Present Invention

The mitochondrial cells obtained by the above-mentioned method are culturable cells with no nucleus, showing mitochondrial activity.

As used herein, "With no nucleus" means preferably having neither nuclear structure nor nuclear DNA. Further, as used herein, "With no nucleus" means that among the cells, 5% or less, preferably 3% or less, of the cells have a nucleus but the rest cells have no nucleus.

Presence or absence of nucleus can be identified by, for example, hematoxylin-eosin stain. Further, the presence or absence of nucleus, nuclear DNA and mitochondrial activity can be identified by, for example, labeling cell structures with fluorescent dyes that specifically stain nucleus, nuclear DNA and mitochondrial membrane potential, respectively, and observing the cell structure under a fluorescent microscope. The labeling of the respective cell structures with fluorescent dyes and detection under a fluorescent microscope can be performed by usual techniques. The fluorescent dye that labels a nucleus and nuclear DNA includes, for example, SYTO Green. The fluorescent dyes that label the mitochondrial membrane include, for example, MitoTracker and MitoTracker Green. As the fluorescent dyes, those commercially available from Molecular Probes, Inc. and so on may be used.

"Showing mitochondrial activity" as used herein means having a structure that can be labeled with a dye that labels active mitochondrial membrane, such as MitoTracker or MitoTracker Green.

The mitochondrial cell of the present invention can be continuously cultured. The culture can be performed in accordance with usual cell culture means. "Culturable" as used herein means that when cells are cultured under medium conditions that are suited for culturing usual mitochondrial cells, cultured cells are proliferated and maintained for 3 months or more, preferably for 6 months or more and more preferably 1 year or more.

Specifically, for example, the mitochondrial cells of the present invention can be cultured in a Dulbecco's modified Eagle medium (D-MEM) containing 10% fetal bovine serum (FBS) at 37° C. in a humidified gas mixture containing 8% $CO_2$.

Note that the methods of preparation of cells from the tissue, of cell culture, of PCR, of preparation of a PCR primer, of preparation of mitochondria and nuclear DNA and so forth used in the present invention can be performed in accordance with usual genetic engineering techniques well-known by one skilled in the art.

(3) Screening Method of the Present Invention

The mitochondrial cells of the present invention have no nucleus, show mitochondrial activity and are culturable so that they are useful as a screening system for developing therapeutic drugs for mitochondria-associated diseases.

Specifically, the mitochondrial cells of the present invention can be used in a screening system for therapeutic drugs for mitochondria-associated diseases, for example, as follows. That is, the mitochondrial cells of the present invention obtained from cybrids between nucleus-less cells having mtDNA derived from patients with the disease of interest and mtDNA-less cultured cells derived from cancer cells are divided into a test cell group and a control cell group. Then, a testing therapeutic drug is administered to the test cell group. After that, the mitochondrial membrane potential activity and so on of the test cell group and control cell group are measured and the groups are compared with each other to study the effect of the therapeutic drug. Thus, screening of a therapeutic drug for mitochondria-associated diseases can be performed. Preferable examples of such therapeutic drugs include therapeutic drugs for mitochondrial diseases, Alzheimer dementia or Parkinson's disease.

According to the present invention, a culturable mitochondrial cell with no nucleus, showing mitochondrial activity has been developed. Up to now, none have reported this kind of cell type with active mitochondria but without nucleus.

It should be emphasized that this result has not been obtained by only one unusual cell culture, but those mitochondrial cells have been obtained repeatedly from the cybrids with or without the pathogenic mutant.

Since platelets have active mitochondria without nucleus, some properties may be transmitted to the mitochondrial cells from the grandparental platelets. However, the nuclear DNA of the parental stem cells must have been derived from Hela cells. Some signals may stimulate Hela nucleus from cytosol or mitochondria. This mitochondrial cell will be very useful to investigate how the nucleus disappeared, what are the signals and how mitochondria are maintained. In addition, these may be applicable for investigating the role of mutant mitochondria, as the cybrids have been to exclude effects of nuclear backgrounds.

EXAMPLES

Hereinafter, the present invention will be described in more detail by examples. However, the present invention should not be considered to be limited thereto unless they are beyond the subject matter of the invention.

Example 1

Preparation of a Cybrid Obtained by Cell Fusion of mtDNA-Less Hela Cell and Platelet and a Floating Cell Derived from the Cybrid To investigate the role of a pathogenic point mutation at nucleotide number 9176 (T9176C) of the mitochondrial genome DNA, cybrid cell lines were constructed by fusing mtDNA-less Hela cells with platelets from healthy control and patients with Leigh syndrome.

(1) $Rho^0$ Cell Culture

Human Hela cell lines depleted of mtDNA (mtDNA-less $Rho^0$ cells) were cultured in Dulbecco's modified Eagle medium (D-MEM) (GibcoBRL. U.S.A.) supplemented with 10% fetal bovine serum, 50 U/ml penicillin, 50 µg/ml streptomycin, 0.2 mM uridine, 2 mM glutamine and 1 mM sodium pyruvate at 37° C. in a humidified gas mixture containing 8% $CO_2$.

(2) Preparation of Platelet

Blood samples were obtained from two siblings showing Leigh syndrome, both of whom had a T9176C mutation of the mitochondrial ATPase 6 gene, and reference blood samples were obtained from two healthy volunteers, a 45-year-old man and a 30-year-old woman. Both volunteers provided informed consent to participate in the research. The siblings were an 18-year-old female and a 13-year-old male whose parents had agreed to the use of their cells for this research. Clinical details of those cases have been reported previously (Makino M et al. Neuromuscular Dis 8: 149–151, 1998; Nakano K et al. Japanese Society for Inherited Metabolic Diseases 15: 217, 1999 (abstract) (Japanese)).

Platelet isolation was performed within two hours of obtaining the blood samples, as reported previously (Shults C W et al. Neurology 50: 193–195, 1998). Briefly, the isolation was performed as described below. 20 ml whole blood with 2 ml volume of 4.5% citrate was obtained. The blood was centrifuged at room temperature for 10 minutes at 200 g, thereby producing platelet rich plasma in two-thirds of the supernatant. The platelet rich plasma was collected and centrifuged again for 30 minutes at 3000 g. The pellet rich in platelet was washed and then collected.

(3) Platelet-Fused Cybrids

Platelet-fused cybrids were obtained according to a previously reported method (Ohta S. Japanese Cell Technology 5 (2): 160–165, 1986). A total of $5 \times 10^7$ $Rho^0$ cells were collected after addition of 0.05% tripsin-EDTA, and were suspended with Hank's buffer. The suspension was gently added to the platelet pellet followed by centrifugation for 10 minutes at 200 g. The pellet was considered to be consisted of mixed platelets and Rho⁰ cells. Next, 0.2 ml of 0.1% ethylenglycol (DMSO) was added thereto for 30 seconds twice, followed by 30 seconds rest at room temperature. Then, 4 ml of D-MEM without fetal bovine serum were added and slowly mixed with the pellet, and the whole was allowed to stand for 10 minutes at room temperature. The mixed buffer was decanted to 40 ml of D-MEM with 10% fetal bovine serum (FBS). The cells were cultured in 96 wells. Colonies of monoclonal platelet-fused cybrids were cultured in each well with buffer exchanged every three days. Monoclonal platelet-fused cybrid cell lines were established.

The obtained cybrid cell lines were isolated (five control and 41 T9176C-mutation cell lines). Cell line 1 was obtained from the older sister of the patients with Leigh syndrome who had the T9176C mutation. Cell line 2 was from the younger brother of the Leigh syndrome patients with the T9176C mutation. Cell line 3 was from the controls. The cybrids initially proliferated showing an adherent form, and the proliferating cell overlay the adherent cells. The overlying cells were separated from the adherent cells and floated in the medium as overgrowth proceeded. The floating cells derived from the cybrid-cell lines were collected and continued to be cultured in fresh D-MEM medium supplemented with 10% FBS at 37° C. in a humidified gas mixture containing 8% $CO_2$. The above-mentioned floating cells have been continuously and acceleratively proliferated for approximately 1 month and have been continued to be proliferated under the same conditions for one and half year.

Example 2

DNA Analyses of Floating Cells

It was confirmed that the floating cells were indeed originated from the cybrid cells that had been obtained by fusing platelets and Rho⁰ Hela cells.

(1) DNA Analyses

Genomic DNA was extracted from the cybrids derived from the platelets of controls and patients with the T9176C mutation, and mitochondrial cells that are derivatives thereof, employing an ordinary method. Detection of the T9176C mutation was performed with the polymerase chain reaction-restriction polymorphism (PCR-RFLP) analysis by a previously described method (Makino M et al. Neuromuscular Dis 8: 149–151, 1998; Thyagarajan D et al. Ann Neurol 38 (3): 468–72, 1995; Campos Y et al Neurology 49: 595–597, 1997). A 178-base pair (bp) fragment of mtDNA encompassing the mutation was amplified using oligonucleotide primers corresponding to mtDNA positions 9025–9046 (forward) GGCCACCTACTCATGCACCTAA (SEQ No. 1) and 9203–9177 (reverse) GTGTTGTCGTG-CAGGTAGAGGCTTCCT (SEQ No. 2), with a T-to-C mismatch at 9179, 3 bp from the 3' end of the fragment. The mtDNA base number was determined according to a literature Anderson et al (Anderson S. et al. Nature 290: 457–465, 1981). PCR was performed under the reaction condition of 35 cycles of: 94° C. for 1 minute; 60° C. for 1 minute; and 72° C. for 1 minute. The PCR products were digested with 15 U of ScrfI for 24 hours at 37° C., electrophoresed through 3% agarose gel and stained with ethidium bromide. In the mutant mtDNA, the mismatch-containing primer introduces a restriction site for ScrfI at nt 9176. Thus, ScrfI cleaves mutant mtDNA into two fragments of 151 bp and 27 bp, whereas ScrfI does not cleave wild type mtDNA and a 178 hp size fragment remains.

According to PCR-RFLP analysis to detect the T9176C mutation, the floating cells derived from the cybrids with the T9176C mutation have the mutation as shown in FIG. 1. On the other hand, the other floating cells derived from the control platelet-fused cybrids have the wild-type mtDNA at base position 9176 (FIG. 1). The floating cells and their original cybrid cells were confirmed to have mtDNA derived from the platelets of the patient and control.

Hereinafter, a description will be made on results shown in FIG. 1.

FIG. 1 shows restriction fragment length analysis results of the T9176C mutation in novel mitochondrial cells. In the presence of this mutation, the 178 bp-amplified fragment was cut by ScrfI into the fragments of 151 bp and 27 bp (the 27-bp fragment is not shown here), whereas wild-type mtDNA remained uncut and was 178 bp. Lanes 1–10 show the 151-bp fragment having the T9176C mutation, while lane 11 shows the 178-bp fragment which does not have the T9176C mutation. Lanes 1–5 represent a sample of a cell line 1 derived from the platelets of the older sister of the Leigh syndrome patients with the T9176C mutation. Lanes 6–10 represent a sample of a cell line 2 derived from the platelets of the younger brother of the cell number 1. Lane 11 represents a sample of a cell line 3 (control) Lane M is a size marker of psi174/Hind III.

Example 3

Characteristics of the Floating Cells

An intracellular structure of floating cells was confirmed by hematoxylin-eosin staining.

The floating cells did not adhere, but loosely aggregated. On microscopy, the cell surface had a rough membranous structure (FIG. 3B). The hematoxylin-eosin stained cytosol had a homogenous eosin color, but there was surprisingly no hematoxylin staining, suggesting the absence of nucleus (FIG. 2A). In contrast, the original cybrid cells had apparent nuclear structure stained by hematoxylin (FIG. 2B). The result suggests that most of the floating cells lack in nuclear structure and nuclear DNA.

Hereinafter, a description will be made on results shown in FIG. 2.

Figure 2:
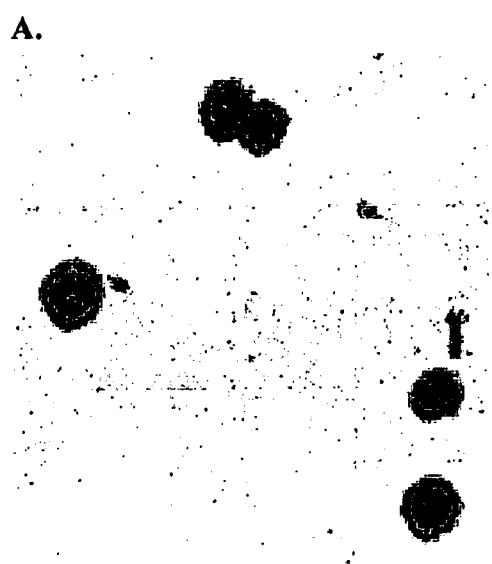
FIG. 2 is a series of diagrams (photographs) showing microscopic characteristics of floating cells.
Figure 2:

FIG. 2 shows microscopic features of the floating cells. The cell line was line 2 (derived from platelets of the younger brother of the Leigh syndrome patients with the T9176C mutation of mtDNA)

(a) The mitochondrial cells lack in nucleus. The cells were stained with hematoxylin-eosin at a magnification of 20× (right). The hematoxylin-eosin stained cytosol had a homogenous eosin color, but there was surprisingly no hematoxylin staining.

(b) As the positive control, the original cybrid cells stained nucleus with Hematoxylin-eosin at a magnification of 20× (right).

Hereinafter, a description will be made on results shown in FIG. 3.

Figure 3:
FIG. 3 is a series of photographs showing results of confocal microscopic analysis of floating cells and original cybrids stained with a variety of dyes.
Figure 3:
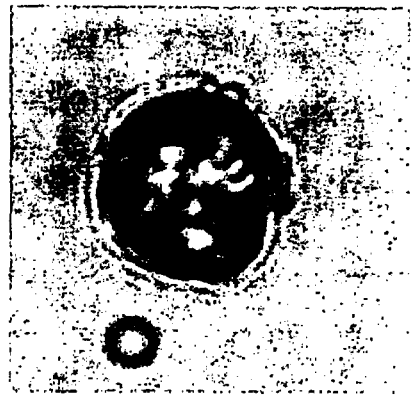
Figure 3:
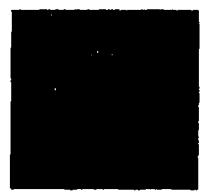
Figure 3:
Figure 3:
Figure 3:
Figure 3:
Figure 3:
Figure 3:
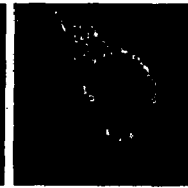
Figure 3:
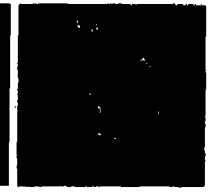
Figure 3:
Figure 3:
Figure 3:
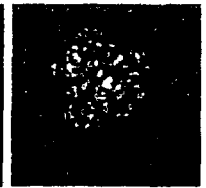
Figure 3:
Figure 3:
Figure 3:
Figure 3:
Figure 3:
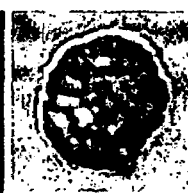
Figure 3:
Figure 3:

FIG. 3 shows results of confocal microscopic analysis for the floating cells and the original cybrids.

FIGS. 3A and 3B show the wild type floating cells containing mitochondrial membrane potential as judged by MitoTracker fluorescent dye. (magnification 60×).

(a) White granular particles were distributed in the cells. Their shape and size are identical to those of mitochondria of the cybrids.

(b) The floating cell on transparent microscopy test revealed a membranous surface.

Example 4

Confocal Measurement with MitoTracker Fluorescent Dye MitoTracker and MitoGreen Double Stain, and MitoTracker and SYTO Green Double Stain An intracellular structure of a floating cell was further confirmed by fluorescent dye staining using a confocal fluorescent microscope.

(1) MitoTracker, MitoTracker Green, and SYTO Green Nucleic Acid Stain Using a Confocal Fluorescencent Microscope MitoTracker CTX-Ros probe (hereafter referred to as MitoTracker) (Molecular Probes. Inc., Oregon) is a lipophilic cationic dye derived from X-rosamine, showing mitochondrion-selective dye that is well retained during cell fixation when measuring mitochondrial membrane potential. MitoTracher Green (Molecular Probes, Inc., Oregon) is also mitochondrion-selective without enhancing mitochondrial membrane potential (Ligon L A et al. J Comp Neurol 427: 340–350, 2000; Hollinshead M et al. J Histochem Cytochem 45: 1053–1057, 1997). SYTOGreen (Syto 16) (Molecular Probes, Inc. Oregon) is a fluorescence dye that can be subjected to nucleic acid stain even in viable cells (Frey T. Cytometry 21: 265–274). The samples to which respectively 20 nM MitoTracker, 20 nM MitoTracker and 100 nM MitoTracker Green, and 100 nM MitoTracher Green and 1 µM SYTO Green were added, were left standing for fifteen minutes. The sectional scans with MitoTracker mono-dye, with MitoTracker and MitoTracker Green double dyes and with MitoTracker and SYTO Green double dyes were obtained using a computer-assisted confocal fluorescent microscope (Fluoview FV300, Olympus, Tokyo) for analysis of the intercellular structure.

MitoTracker CTX-Ros (hereafter referred to as MitoTracker) shows a mitochondria-specific mitochondrial membrane potential. The floating cells were dyed with MitoTracker and were observed with the confocal microscope. As a result, as shown in FIG. 3A, granular particles were distributed in the cells. Their shape and size were identical to those of mitochondria of the cybrids (FIGS. 3E and 3I). The MitoTracker Green dye also labels specifically mitochondria regardless of mitochondrial membrane potential. The double MitoTracker and MitoTracker Green labeling with the confocal fluorescence microscope showed that both of the wild type floating cells and the mutation type floating cells were positively stained with both MitoTracker (FIGS. 3C and 3G) and MitoTracker Green (FIGS. 3D and 3H). The mitochondria in both of the wild type cybrids and the mutation type cybrids surrounding the nucleus were granularly dyed with MitoTracker (FIGS. 3E and 3I) and MitoTracker Green (FIGS. 3F and 3J). A fluorescent dye, SYTO Green stains nucleic acid of nucleus by penetrating membranes into viable cells. The floating cells and the cybrids were labeled with double MitoTracker and SYTO Green dyes with the confocal fluorescence microscope FIGS. 3K-3T. As a result, both of the wild type floating cells and the mutation type floating cells were positively stained with MitoTracker (FIGS. 3K and 3P), but were negatively stained with SYTO Green (FIGS. 3L and 3Q). On the other hand, the original cybrids in the wild type and the mutation type were positively stained with both MitoTracker (FIGS. 3N and 3S) and SYTO Green (FIGS. 3Q and 3T).

Those results strongly suggest that most of the floating cells contain mitochondrial membrane potential, but lack in nuclear structure and nuclear DNA. Thus, the inventors designate those floating cells mitochondrial cells.

Hereinafter, the results shown in FIG. 3 will be described.

FIG. 3 shows the results of confocal microscopic analysis of a floating cell and an original cybrid.

FIGS. 3C-3J. The wild type and mutation type floating cells contained mitochondrial membrane specific to mitochondrion-selective dyes, as the mitochondria of the cybrids did (magnification 100×).

(C, G) Both of the wild type floating cells (C) and the mutation type floating cells (G) revealed granular stain, labeled with MitoTracker, which was specific to mitochondrial membrane potential.

(D, H) Both of the wild type floating cells (D) and the mutation type floating cells (H) revealed granular stain, labeled with MitoTracker Green.

(E, F, I, J) The mitochondria of the wild type cybrids showed granular stains surrounding the nucleus, labeled with MitoTracker dye (E), and MitoTracker Green (F). The mitochondria of the mutation type cybrids also showed granular stains surrounding the nucleus, labeled with MitoTracker dye (I), and MitoTracker Green (J).

FIGS. 3K-3T. Both of the wild type floating cells and the mutation type floating cells lack in nuclear structure and nuclear DNA with double MitoTracker, and SYTO Green dyes (magnification 100×).

(K, P) The floating cells in the wild type (K) and the mutation type (P) revealed granular stains labeled with MitoTracker.

(L, Q) The floating cells in the wild type (L) and the mutation type (Q) revealed negative stains labeled with SYTO Green.

(M, R) The transmission microscopy test revealed a rough membranous surface in the wild type (M) and the mutation type (R) floating cells.

(N, S) Both the wild type cybrids (N) and the mutation type cybrids (S) showed granular stain surrounding the nucleus labeled with MitoTracker dye.

(O, T) The nuclei in the wild type (O) and the mutation type (T). The wild type cybrids were stained with SYTO Green label.

Example 5

Flow Cytometry of Mitochondrial Cells Using SYTO Green and MitoTracker

To examine the presence of nuclei and mitochondria in the mitochondrial cell population, two-color flow cytometry was performed.

After adding 100 nM MitoTracker and 1 µM SYTO Green to mitochondrial cells, the samples were left standing for fifteen minutes. The samples were examined with a flow cytometer (Epics Elite ESP, Beckman Coulter Inc., U.S.A.). Neglecting false positive induced by the other spectrum band in two colors was confirmed with negative control, single label of MitoTracker and SYTO Green. Total cell counts of the mitochondrial cells or the cybrids were around 4,000–8,000.

FIGS. 4A-4D show the results of flow cytometry of normal control cybrid and cybrid with T9176C mutation as well as mitochondrial cells derived from the respective cybrids double stained with MitoTracker and SYTO Green. The results of the flow cytometry were divided into four regions based on positive or negative staining of SYTO Green or MitoTracker. 97.6% of the T9176C mutation type mitochondrial cells and 99.6% of wild type mitochondrial cells were present in the SYTO Green negative region. On the other hand, 92.4% of the T9176C mutation type cybrids and 97.3% of the wild type cybrids were present in the SYTO Green and MitoTracker positive regions, respectively. Those results suggest that most mitochondrial cells lack in nucleus but only less than several % of cells maintain nucleus and nuclear DNA.

Mitochondrial membrane potential with MitoTracker was compared between T9176C mtDNA mutation strain and wild-type mtDNA strain in the mitochondrial cells and the cybrids (FIGS. 4E and 4F). The mitochondrial cells with T9176C mutation mtDNA had less active mitochondrial potential than that of the mitochondrial cells with wild-type mtDNA. The intensity of MitoTracker in the mutation type mitochondrial cells was 17.4±20.4 (Mean±standard deviation), while 37.8±30.9 in the wild type ones. The result was comparable to the difference between T9176C mtDNA mutation strain and wild-type mtDNA strain in the cybrids. The intensity was 43.5±79.9 in the mutation cybrids, while 101.6±71.7 in the wild type ones. The cybrids with T9176C mutation mtDNA had also less active mitochondria than those of the cybrids with wild-type mtDNA. This observation indicates that T9176C mtDNA mutation affects a decrease of mitochondrial membrane potential regardless of existence of nucleus.

Hereinafter, a description will be made on results shown in FIG. 4.

Figure 4:
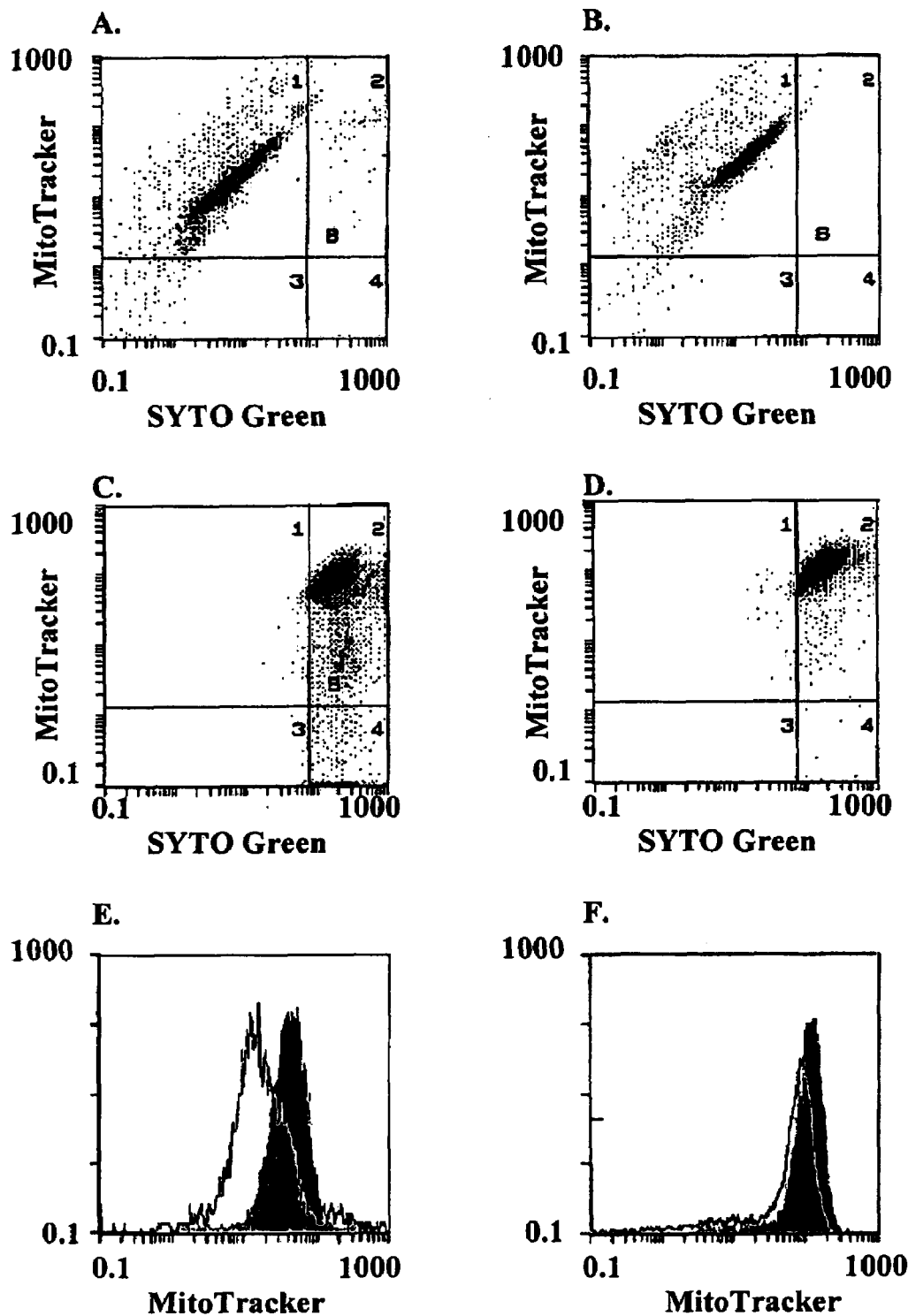
FIG. 4 shows results of flow cytometry in mitochondrial cells and original cybrids stained with SYTO Green and MitoTracker dyes.

FIG. 4 shows results of flow cytometry in mitochondrial cells and original cybrids stained with SYTO Green and MitoTracker dyes.

(A) Mitochondrial mutation type cells. (B) Mitochondrial wild type cells. (C) Mutation type cybrids. (D) Wild type cybrids.

FIGS. 4A-4D The mitochondrial cells lack in nucleus or most nuclear DNA, while they keep mitochondrial membrane potential. The areas were divided into four parts depending on positive or negative of SYTO Green and MitoTracker. The standard of positive or negative was defined according to negative control and single staining of the cybrids. 97.6% of T9176C mutation type mitochondrial cells (A) and 99.6% of wild type mitochondrial cells (B) existed in the SYTO Green negative area, which were constructed by no. 1 and 3 areas in each figure. On the other hand, 92.4% of T9176C mutation type cybrids (C) and 97.3% of wild type cybrids (D) existed in both SYTO Green and MitoTracker positive area, which was represented in no. 2 area.

FIGS. 4E and 4F. The mitochondrial cells with T9176C mutation mtDNA revealed less active mitochondrial membrane potential as evaluated by MitoTracker than those of the mitochondrial cells with wild-type mtDNA as well as the cybrids.

(A) The left open curve is the intensity of the mutation type mitochondrial cells. The right closed black curve is that of the wild type ones.

(B) The left open curve is the intensity of the mutation type cybrids. The right closed black curve is that of the wild type ones.

Example 6

Proliferation Test of Mitochondrial Cells
Proliferation of mitochondrial cells was considered.

(1) Sorting of Mitochondrial Cells Using a Flow Cytometer

Both the mtDNA mutation type and wild type mitochondrial cells were used as samples. The wild type mtDNA cybrid was used as control. 1 µM of Syto Green (Syto 16) (Molecular Probes Inc., Oregon) specific to nucleic acids of viable cells was added to the sample and the whole was left to stand for 15 minutes and stained by fluorescent dye. Then, sorting was carried out on the resultant product by using a flow cytometer (Epics ALTRA (trademark) HyperSort (trademark), Beckman Coulter Inc., United States). Sorting was carried out on the mutation type and wild type mitochondrial cells with fluorescence intensity of nuclear staining of original cybrid cells for the mitochondrial cells as a reference so that a cell having fluorescence intensity comparable to the reference was classified into a nuclear DNA-containing group and a cell having fluorescence intensity below the reference was classified into a nuclear DNA non-containing group.

(2) The Cell Count

The sorted mitochondrial cells were cultured in fresh RPMI 1640 medium supplemented with 10% FBS at 37° C. in a humidified gas mixture containing 8% $CO_2$. The control cybrids were also cultured under the same condition except that DMEM medium was used instead of RPMI after exposure to SYTO Green. The number of cells was counted with passage of time with respect to the nuclear DNA-containing group and the nuclear DNA non-containing group with dye exclusion test using trypan blue dye (every two weeks).

As a result of the tests, like the nuclear DNA-containing group, the nuclear DNA non-containing group also proliferated FIGS. 5A and 5B. However, the proliferation rate of the nuclear DNA-containing group was faster than that of the nuclear DNA non-containing group FIG. 5A. The present studies suggest that the mitochondrial cells can proliferate in the cell group in a state where the amount of nuclear DNA is very low. That is, the present studies suggest that the mitochondrial cells can proliferate without nucleus.

Hereinafter, the results shown in FIG. 5 will be described.

Figure 5:
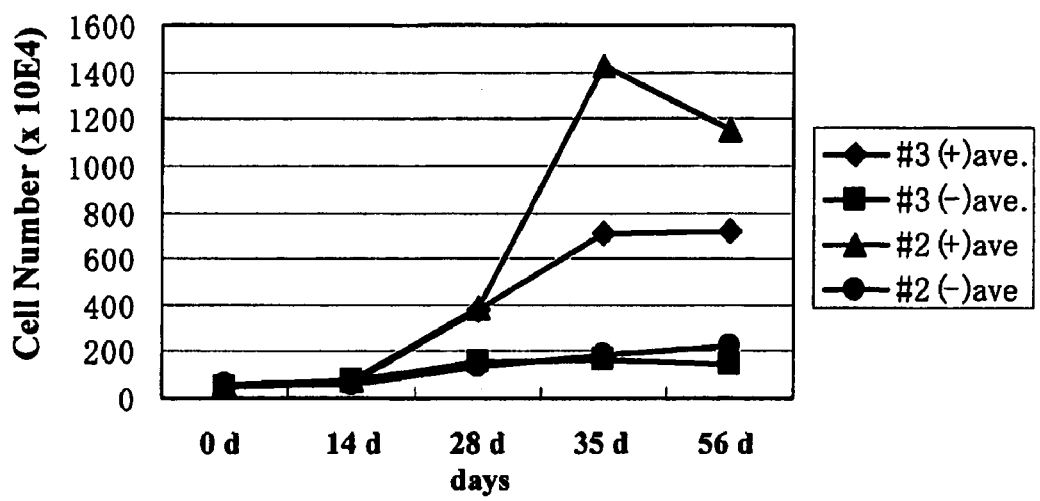
FIG. 5A and FIG. 5B are diagrams showing results of proliferation tests on mitochondrial cells.
Figure 5:
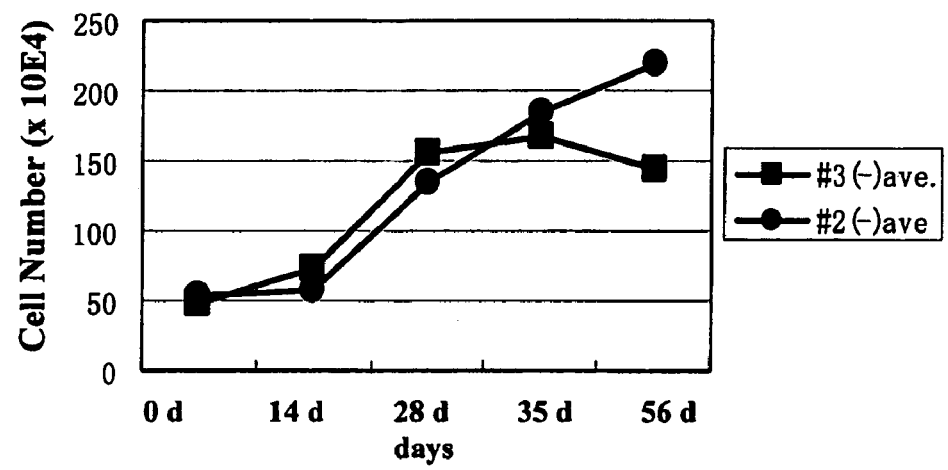

FIG. 5 shows the results of proliferation test of mitochondrial cells. Reference symbol #3(+) designates a nuclear DNA-containing group of wild type mitochondrial cells and reference symbol #3(−) designates a nucleus non-containing group. Reference symbol #2(+) designates a nuclear DNA-containing group of T9176C mutation type mitochondrial cells while reference symbol #2(−) designates a nucleus non-containing group. The number of cells in each group was counted with passage of time by Trypan blue stain.

What is claimed is:

1. A method of producing a culturable cell population, showing mitochondrial activity, wherein the cell population contains at least one cell with a nucleus and cells with no nucleus, and wherein 95% or more among the cell population are cells with no nucleus, comprising:
   performing cell fusion between a nucleus-less cell having mitochondrial DNA and a mitochondrial DNA-less cultured cancer cell or cell of an established cell line;
   culturing resulting cybrid cells; and
   recovering floating cells which separate from adherent cybrid cells during the culture thereof.

2. A method according to claim 1, wherein the nucleus-less cell having mitochondrial DNA is a platelet.

3. A method according to claim 1, wherein the mitochondrial DNA-less cultured cell is a Hela Rho$^0$ cell.

4. A culturable cell population, showing mitochondrial activity obtained by the method according to any one of claims 1 to 3.

5. A method of producing a population of cells with no nucleus showing mitochondrial activity, comprising:
   performing cell fusion between a nucleus-less cell having mitochondrial DNA and a mitochondrial DNA-less cultured cancer cell or cell of an established cell line;
   culturing resulting cybrid cells;
   recovering floating cells which separate from adherent cybrid cells during the culture thereof;
   determining the presence or absence of a nucleus in the floating cells; and
   selecting cells with no nucleus.

* * * * *